United States Patent [19]

Weissman

[11] 4,303,391

[45] Dec. 1, 1981

[54] DENTAL BORE-LOCATING GUIDE

[75] Inventor: Bernard Weissman, New York, N.Y.

[73] Assignee: IPCO Corporation, White Plains, N.Y.

[21] Appl. No.: 121,834

[22] Filed: Feb. 15, 1980

Related U.S. Application Data

[63] Continuation-in-part of Ser. No. 70,247, Aug. 27, 1979, Pat. No. 4,260,383.

[51] Int. Cl.³ .............................................. A61C 3/02
[52] U.S. Cl. ..................................................... 433/76
[58] Field of Search ..................... 433/72, 225, 75, 76

[56] References Cited

U.S. PATENT DOCUMENTS 3,414,975 12/1968 Small .................................... 433/75

Primary Examiner—Robert Peshock
Attorney, Agent, or Firm—Friedman, Goodman & Teitelbaum

[57] ABSTRACT

A dental guide for locating suitable positions at which bores are to be drilled in teeth for receiving a dental retaining splint, the guide being formed of a material which is detectable under x-rays. The guide includes a continuous rod shaped into a configuration having a U-shaped front section for overlying the labial surface of the teeth. The legs of the U-shaped front section extend into laterally disposed arms for overlying the occlusal surface of the teeth, and the arms terminate in downwardly extending pins. Each of the pins respectively is disposed in a common plane with an associated one of the legs of the U-shaped front section. With the pins positioned in drill guides, an x-ray taken of the teeth will reveal the location of the legs of the U-shaped section with respect to the teeth, so that a proper orientation of the bores to be drilled can be determined.

11 Claims, 4 Drawing Figures 4,303,391

DENTAL BORE-LOCATING GUIDE

RELATIONSHIP TO OTHER APPLICATIONS

This application is a continuation-in-part application to U.S. Ser. No. 70,247 filed on Aug. 27, 1979 now U.S. Pat. No. 4,260,383 issued Apr. 7, 1981 for "Dental Retaining Splint" by the same applicant, the disclosure of this application being incorporated herein by reference.

BACKGROUND OF THE INVENTION

This invention relates to dentistry in general, and more particularly to a dental guide for locating suitable positions on teeth at which bores are to be drilled for receiving a dental retaining splint.

The use of splints for reinforcement and retention of dentition is known in the field of dentistry. However, the use and application of such splint structures has been complex and difficult, and accordingly, has been restricted to specific locations in the mouth. For example, some splint structures are restricted for use only on the lingual surfaces of posterior teeth. Other splint structures require special equipment in order to assure the required horizontal paralelisms.

A procedure for overcoming and simplifying the use of dental splints has been provided in the aforementioned co-pending parent application. In such application, there are described dental retaining splints having an elongated bar-like member with a plurality of upwardly extending tubular members. The tubular members have axial openings extending therethrough which serve as drill guides. In the dental procedure, the splint is first temporarily held in a channel provided in adjacent teeth in a conventional manner, with the tubular members extending upwardly. The tubular members function as guides for a drill to thereby form pilot holes in the teeth. After the pilot holes are formed, the splint is removed and the pilot holes function as lead holes for the formation of enlarged bores. Subsequently, the splint is replaced in the channel so that the tubular members are disposed in the bores, and then an inlay fills in the channel to cover the splints.

In utilizing such splints, the bores must be drilled through the occlusal surfaces of the teeth and into the teeth enamel. However, it is preferable that the bores be drilled with such an orientation as to avoid penetrating the pulp tissue contained in the tooth. Since the dental splint straddles at least two adjacent teeth, if properly placed, it is possible to drill the bores in such a manner that they are spaced inwardly of the pulp tissue. However, the problem is that until the bores are drilled, it is generally not known whether the bores will penetrate the pulp tissue or not.

SUMMARY OF THE INVENTION

Accordingly, it is an object of the present invention to provide a dental locating tool which is useful in determining the orientation of bores to be drilled in the teeth.

Another object of the present invention is to provide a dental guide for locating suitable positions on the teeth at which bores are to be drilled.

A further object of the present invention is to provide a dental locating guide which can be used in conjunction with a dental splint of the type described in the aforementioned co-pending parent application.

Still another object of the present invention is to provide a dental locating guide which can be used for positioning bores to be drilled so as to avoid penetration of the pulp tissue in a tooth.

Yet another object of the present invention is to provide a dental locating guide which can be inserted into a dental retaining splint of the type described in the aforementioned parent application, and which can be used to suitably determine the proper location of the dental splint to drill bores at desired orientations within the teeth.

A further object of the present invention is to provide a procedure for locating bores to be drilled in the teeth, which bores will receive a dental splinting member.

An added object of the present invention is to provide a dental locating guide which is easy to use, accurate in its determination, and simple to manipulate.

These objects are achieved in accordance with a preferred embodiment of the present invention wherein the dental bore-locating guide comprises a front member formed of a material which is detectable under x-rays for overlying a portion of the labial surface of at least one tooth. A top member laterally extends from the front member for overlying a portion of the occlusal surface of the tooth. A pin extends from the top member and lies in a common plane with the front member. The pin is received in a tubular drill guide which upwardly extends from the occlusal surface of the tooth. With the pin positioned in the drill guide, an x-ray taken of the tooth will reveal the location of the front member with respect to the tooth, which location will represent the orientation of the bore to be drilled.

In a preferred embodiment of the invention, the locating guide includes a continuous rod having a U-shaped configuration to form the front member. The top member represents arms extending from the top ends of the legs of the U-shaped member, and there is a respective pin depending from the ends of each arm to thereby form a double-U configuration.

The invention also provides for a method of locating bores to be drilled in the teeth. The method includes the positioning of a drill guide on the occlusal surface of the teeth with the tubular guiding portions of the drill guide extending upwardly therefrom. The pin portions of a locating guide are inserted into the tubular guiding portions. The arms of the locating guide extend over the occlusal surface, and a front U-shaped portion of the locating guide overlies the labial surface. The legs of the U-shaped portion of the locating guide are co-planar with their respective pins. An x-ray is then taken of the teeth while the locating guide is positioned. Based upon the location of the legs of the U-shaped member of the locating guide with respect to the teeth, the orientation of the resulting bores to be drilled can be determined.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which.

DETAILED DESCRIPTION OF THE PREFERRED EMBODIMENT

Figure 1:
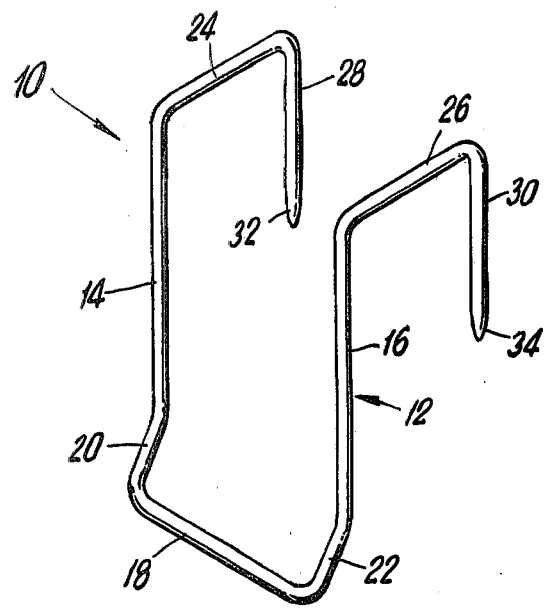
FIG. 1 is a perspective view illustrating the dental bore-locating guide in accordance with the present invention.
Figure 2:
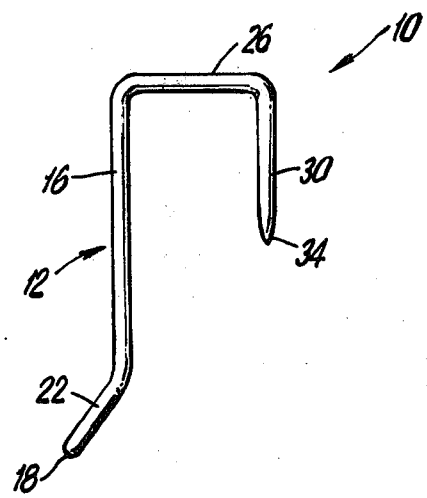
FIG. 2 is a side view of the dental bore-locating guide shown in FIG. 1.

Referring now to the drawings, FIGS. 1 and 2 show a dental bore-locating guide 10 in accordance with the present invention. The locating guide 10 comprises a front section 12 formed into a substantially U-shaped configuration and includes the leg portions 14 and 16 interconnected by a transverse bight section 18. The bight section, as well as the lowermost parts 20, 22 of the respective leg portions 14, 16, is flared outwardly in a forward direction. The upper ends of the respective leg portions 14, 16 have laterally extending arms 24, 26 which terminate in downwardly depending pins 28, 30. The free ends of the pins terminate in points 32, 34.

The leg portions 14 and 16 are parallel to each other, the arms 24, 26 are parallel to each other, and the pins 28, 30 are parallel to each other. Furthermore, the arms 24, 26 are perpendicular to both their respective leg portions 14, 16 and pins 28, 30. Additionally, the leg portion 14 is parallel to the pin 28, and the leg portion 16 is parallel to the pin 30. It is noted, that the leg portion 14, the arm 24 and the pin 28 are disposed in a first plane; and the leg portion 16, the arm 26 and the pin 30 are disposed in a second parallel plane. Accordingly, the pins 28, 30 are disposed in a third plane which is perpendicular to the above mentioned first and second planes, so that the leg portions 14, 16 are directly in front of respective ones of the pins 28, 30.

Figure 3:
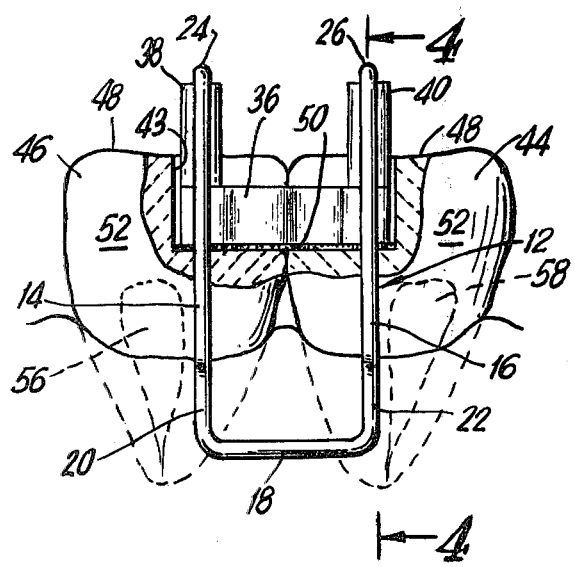
FIG. 3 is an elevational view, partly in cross section, illustrating the positioning of the dental bore-locating guide, in combination with a dental retaining splint, in order to determine the orientation of the bores to be drilled for the dental retaining splint.
Figure 4:
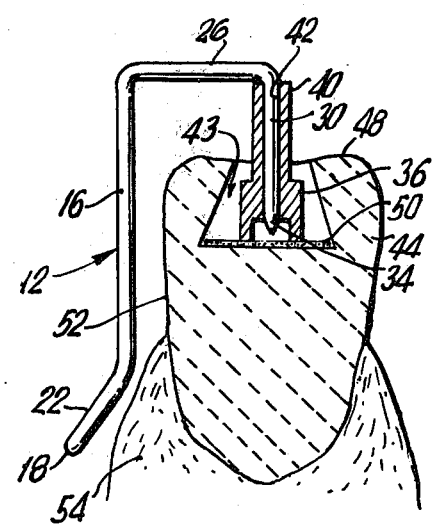
FIG. 4 is a side sectional view taken along line 4—4 of FIG. 3.

Referring now to FIGS. 3 and 4, the dental bore-locating guide of the present invention will be shown in use, in combination with a dental retaining splint of the type described in the aforementioned parent application. As was described in the parent application, the dental retaining splint comprises a bar-like body member 36 including a plurality of hollow tubular members 38, 40 extending perpendicularly therefrom. The tubular members have axial openings 42 formed therethrough. In the dental procedure, the splint is first temporarily held in a channel 43 provided in adjacent teeth 44, 46, with the tubular members extending upwardly therefrom. The channel is formed in the occlusal surfaces 48 of the teeth 44, 46 and is substantially wider and deeper than the bar-like body member 36.

The tubular members 38, 40 serve as guides for a drill (not shown) in order to form pilot holes in the teeth. The drill is initially inserted through the tubular members one at a time, and then drilled into the tooth enamel to form the pilot holes. The dental splint is then removed and the pilot holes function as lead holes for the formation of enlarged bores in order to receive the tubular members therein for retaining the adjacent teeth in a fixed position relative to each other. When the splint is repositioned in the channel, the tubular members are disposed downwardly in the enlarged bores, and then an inlay fills in the channel to cover the splint.

When drilling the bores, it is required that they should not penetrate into the pulp tissue of the teeth. However, with the dental splint positioned at the upper surface of the teeth, it is not readily known whether the bores to be drilled will penetrate the pulp tissue or not.

Utilizing the dental bore-locating guide 10 of the present invention, the dental splint is positioned in the channel and temporarily held by means of wax 50. However, since the channel 43 is substantially larger than the splint, there is sufficient room to move the splint both laterally as well as longitudinally within the channel.

Accordingly, an initial position of the dental splint is presumed and the splint is temporarily retained in place by means of the wax 50. The dental bore-locating guide 10 of the present invention is then inserted with the pins 28, 30 respectively being positioned in the upwardly extending tubular members 38, 40. The arms 24, 26 extend across the occlusal surface so that the U-shaped member is positioned in front of the labial surface 52 of the teeth. The outwardly flared bight portion 18 will accommodate the wider gum tissue 54 located beneath the teeth.

With the dental bore-locating guide 10 positioned in the dental retaining splint, as shown in FIGS. 3 and 4, an x-ray is taken of the teeth. The locating guide is formed of a material which will be detectable under x-rays. For example, the locating guide can be formed of a metal rod. The x-rays will therefore reveal the inner structures of the teeth, and specifically, the pulp tissue 56, 58. It will also show the relative position of the leg portions 14, 16 with respect to said pulp tissues 56, 58.

As shown in FIG. 3, the leg portions 14, 16 are shown adjacent to, but not penetrating, the pulp tissues 56, 58. Accordingly, since the leg portions 14, 16 are co-planar with the pins 28, 30 which in turn are located in the axial openings 42 in the tubular members 38, 40, the bores that will be ultimately drilled will have the same orientation in the teeth 44, 46, as do the leg portions 14, 16.

If, on the other hand, the x-rays were to show that one of the leg portions 14 or 16 was such as to cross one of the pulp tissues 56, 58, then it would be required to re-orient the position of the dental splint by moving it longitudinally in the channel 43 so as to prevent the bores from entering into the pulp tissues 56, 58.

Even before the x-rays are taken, the locating guide 10 can be used as an initial visual inspection, which can determine whether the bight section 18 is lying horizontally or whether it is skewed. A skewed bight section 18 will indicate that one end of the bar-like member 36 is positioned upwardly from the bottom of the channel 43. This could mean that the channel is not horizontal or that there is an interference contained in the channel which has gone undetected and which is preventing a suitable placement of the bar-like member directly adjacent the bottom of the channel. Also, a visual inspection will determine whether the leg portions 14, 16 are suitably positioned with respect to the exterior of the teeth. Accordingly, these above conditions would be corrected before taking the x-rays, and obviously before performing any drilling operation.

Although the locating guide 10 has only been described in connection with the formation of two adjacent holes, it is understood that it can also be used with an elongated bar-like member having a body section extending over more than two teeth, whereby more than two bores would be required to be drilled. It can also be used with a bar-like member having more than two tubular sections. Specifically, the present invention would find a suitable location of two bores and could then be used in a leap-frog manner to find the suitable orientation of the other bores. Alternately, the present locating guide could be expanded so as to include more than two legs so that it could span more than the two teeth and thereby be used to position simultaneously three or more bores, as is required for the specific dental splint being utilized.

Nemerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dental bore-locating guide comprising:
    front member means for overlying a portion of the labial surface of at least one tooth, said front member means being detectable under x-rays, said front member means including a pair of parallel legs connected by a bight to define a U-shaped section;
    top member means laterally extending from said front member means for overlying a portion of the occlusal surface of the tooth, said top member means including a pair of parallel arms perpendicularly extending from respective ends of said legs;
    pin means extending downwardly from said top member means and lying in a spaced plane from said front member means for being received in a tubular drill guide upwardly extending from the occlusal surface of the tooth, said pin means including a pair of parallel pins perpendicularly extending from respective ends of said arms;
    associated, connected ones of said legs, arms and pins defining a first U-shaped unit;
    the other associated, connected leg arm and pin defining a second U-shaped unit;
    said bight connecting said first U-shaped unit to said second U-shaped unit to define a double U-configuration;
    whereby with the pin means positioned in the drill guide, an x-ray taken of the tooth will reveal the location of the front member means with respect to the interior of the tooth so that a proper orientation of the bores to be drilled can be determined.

2. A bore-locating guide as in claim 1, wherein said double U-configuration is a continuous rod.

3. A bore-locating guide as in claim 2, wherein said rod is of metal material.

4. A bore-locating guide as in claim 1, wherein the bight portion of said U-shaped section is outwardly flared to be spaced from the tooth to accommodate the gum tissue.

5. A bore-locating guide as in claim 1, in combination with a drill guide, said drill guide comprising an elongated bar-like member being disposable in a channel extending from a first tooth to at least one adjacent tooth, and tubular members extending perpendicularly from said bar-like member for receiving said pins of said bore-locating guide, said tubular members serving as a guide for a drill during formation of pilot holes in the teeth, said pilot holes functioning as lead holes for the formation of the bores.

6. A bore-locating guide in combination with a drill guide as in claim 5, wherein said drill guide serves as a dental retaining splint with said tubular members being received in the bores.

7. A dental bore-locating guide comprising:
    a U-shaped member having a pair of parallel legs connected by a bight;
    a pair of parallel arms perpendicularly extending from respective ends of said legs;
    a pair of parallel pins perpendicularly extending from respective ends of said arms;
    one of said legs, one of said arms and one of said pins defining a first U-shaped unit;
    the other leg, the other arm and the other pin defining a second U-shaped unit;
    said first U-shaped unit being disposed in a first plane, and said second U-shaped unit being disposed in a second plane parallel to said first plane; and
    said pins being disposed in a third plane perpendicular to said first and second planes so that said legs are directly in front of respective ones of said pins.

8. A bore-locating guide as in claim 7, wherein said guide is a continuous metal rod.

9. A bore-locating guide as in claim 8, wherein said bight is flared outwardly in a direction away from said pins.

10. A method of locating bores to be drilled in teeth, comprising:
    positioning a dental guide having tubular guiding portions on the occlusal surface of the teeth with the tubular guiding portions extending upwardly therefrom;
    inserting pin portions of a locating guide into the tubular guiding portions of the drill guide with arms of the locating guide extending over the occlusal surface toward the labial surface of the teeth, and a front U-shaped portion of the locating guide overlying the labial surface with the legs of the U-shaped portion being co-planar with the respective pin portions;
    taking an x-ray of the teeth having the locating guide positioned within the drill guide, and
    determining the orientation of the bores to be drilled from the resulting x-ray location of the legs of the U-shaped member with respect to the internal structure of the teeth.

11. A method as in claim 10, further comprising the steps of:
    forming a channel across at least two adjacent teeth, and
    temporarily disposing a dental retaining splint having tubular members in said channel, with the dental retaining splint defining the dental guide and the tubular members defining the drill guiding portions.

* * * * *